United States Patent [19]

Wichterle et al.

[11] 4,087,487

[45] May 2, 1978

[54] CARRIERS FOR BIOLOGICALLY ACTIVE COMPOUNDS AND METHODS FOR THE PRODUCTION THEREOF

[75] Inventors: Otto Wichterle; Jiri Coupek, both of Prague, Czechoslovakia

[73] Assignee: Ceskoslovenska akademie ved, Prague, Czechoslovakia

[21] Appl. No.: 670,854

[22] Filed: Mar. 26, 1976

Related U.S. Application Data

[60] Division of Ser. No. 470,006, May 15, 1974, Pat. No. 3,969,436, which is a continuation-in-part of Ser. No. 387,313, Aug. 10, 1973, abandoned.

[30] Foreign Application Priority Data

Aug. 18, 1972 Czechoslovakia ................... 5743-72

[51] Int. Cl.$^2$ ............................................. C08L 33/04
[52] U.S. Cl. ........................... 260/901; 260/29.6 RW; 424/81; 424/81
[58] Field of Search ...................... 260/901, 29.6 RW; 106/15 AF

[56] References Cited

U.S. PATENT DOCUMENTS

| | | | |
|---|---|---|---|
| 3,544,500 | 12/1970 | Osmond et al. | 260/29.6 |
| 3,607,821 | 9/1971 | Clarke et al. | 260/34.2 |
| 3,632,789 | 1/1972 | Heinsheim et al. | 260/33.6 |

*Primary Examiner*—Carman J. Seccuro

[57] ABSTRACT

There is disclosed a method for the production of carriers for biologically active compounds comprising forming a bond by admixing (a) a three dimensional water insoluble diazotizable polymer operative to function as a primary carrier and (b) a water soluble linear polymer having ligands operative to bind said biologically active compounds and operative to function as a secondary carrier, whereby the union of (a) and (b) is operative to serve as a carrier for biologically active compounds and carriers produced in accordance therewith.

8 Claims, No Drawings

CARRIERS FOR BIOLOGICALLY ACTIVE COMPOUNDS AND METHODS FOR THE PRODUCTION THEREOF

This is a Divisional application of Ser. No. 470,006, now U.S. Pat. No. 3,969,436, filed May 15, 1974, which itself is a continuation-in-part of Ser. No. 387,313, filed Aug. 10, 1973, now abandoned.

This invention relates to a method for producing carriers for biologically active compounds and to the carriers so produced.

Methods heretofore employed for the immobilization of soluble enzymes, antigens, antidotes and other soluble biopolymers, especially those having a proteic character, have been reviewed, e.g. in the paper of Silman and Katchalsky (Ann. Rev. Biochem. 35-II, 873 (1966). According to these methods, the biologically active compounds are either transformed into an insoluble three dimensional complex by the action of di- or multifunctional agents, or, in the case of a polyfunctional agent called a "carrier," the biopolymer is tightly held to the surface thereof by strong bonds. The latter method is particularly important in practical application as it enables one to bind the active compound with an artificially prepared polymeric carrier which has a macrostructure suitable for this type of application, e.g. in reaction or chromatographic columns or in various types of medical apparatus.

The biochemical activity of a compound so linked can be more or less disturbed not only by formation of new chemical bonds, but also by fixation at the linked surface, which linking acts to limit the free mobility of the protein molecule and also shields the free access of the substrate attached to the protein. The tertiary structure of a biologically active macromolecule can also be unfavorably affected by binding to a solid surface. It is for this reason that numerous and in part, successful attempts were realized in the formation of more movable although stronger ties between a carrier and a biologically active molecule. P. Cuatrecasas in J. Biol. Chem. 245, 3059 (1970) has described the effects of a manifold increase of capacity of a linked staphylococcus nuclease when a chain of several atoms was inserted between the binding ligand and the carrier skeleton, for instance, sepharose or polyacrylamide.

Rather than look to an intricate synthetic route on how to bind the ligand to a macromolecular structure by means of an extended "arm" which is synthetized in the molecule carrying the ligand, a linear hydrophilic macromolecule already carrying the prepared or preformed ligand is attached to the basic rigid three-dimensional structure of the carrier. In this way, a macromolecular system is formed wherein the molecules of the linear polymer which are movable and reach deeply into a solution are attached to the surface of the three-dimensional network, and thereby provide the system with mechanical strength and elasticity at the cost of blocking the free mobility of its polymeric chains.

Such a system is prepared in a simple experimental way by formation of the basic three-dimensional structure, which may be herein called "the primary carrier," having such reactive sites, which are also able to bind themselves with ligands of the soluble linear "secondary carrier," while the ligands of the secondary carrier are adaptable or already adapted for fixation to the biologically active compounds.

In the capacity of a primary carrier (component $a$) any of the well known carriers of biologically active compound can be applied. These carriers contain reactive groups which are capable to react with reactive counterparts in molecules of proteins: diazonium groups capable to couple with phenolic groups of tyrosine units, organomercuric cations capable to attach to sulfhydryl groups of cystein units, carboxy anhydride, carboxyhalogenide, isocyanate, isothiocyanate azide, nitro fluorophenyl, or aldehyde groups which are capable to form covalent links to amino groups of arginine units. If used as a component $a$ these conventional carriers have to be combined with a component $b$ containing similar counterpart ligands as contained in proteins i.e. sulfhydryl, amino or phenolic functions.

Finally, certain naturally occuring proteinic polymers can be used as a component $a$. Their reactive ligands can find complementary their counterparts in operative functions of the component $b$.

The primary carrier (component $a$) may further suitably be comprised of a macroporous mass which is result of the copolymerization of suitable monomers. For example a monoolefinic hydrophilic monomer such as a lower alkyl ester ($C_1 - C_8$), optimally hydroxysubstituted such as 2-hydroxyethylmethacrylate, glycerol monoacrylate, diethylene glycol monomethacrylate or the like, copolymerized with a cross-linking monomer such as allyl methacrylate, ethylene dimethacrylate, glycerol dimethacrylate, butanetetrole dimethacrylate, N,N'-methylenebisacrylamide or the like and with an operative monomer containing the required reactive group (ligand) or such a group in a preformed state which can be obtained in the polymeric product by chemical modifications. The weight of the monofunctional hydrophilic monomer to the crosslinking monomer is about 1:0.03 to 1:0.45, the weight percent of the operative monomer is ordinarily about 1 to 25%. As an operative monomer containing a preformed ligand 4-nitroacrylanilide or p-acetaminophenoxyethyl methacrylate can be used. In the first case the nitrogroups introduced in the copolymer can be transformed into amino groups by selective reduction with titanous chloride, in the second case the aromatic amino group is obtained by alcaline hydrolysis. The aromatic amino groups can be transformed afterward either by nitrous acid treatment into diazonium groups or by thiophosgene treatment into isothiocyanato groups; further, the aromatic ring can be mercurated in the orthoposition to the aminogroup. Another example of an operative monomer is N-acryloyl-N'-tert-butoxycarbonyl hydrazine the copolymer of which contains after dilute acid treatment free acyl hydrazido groups which can be finally transformed into reactive azido groups by nitrous acid treatment. A further example of an operative monomer is methacryloyl anilide the copolymer of which can be mercurated by treatment with aqueous solutions of mercuric acetate or perchlorate.

The role of operative units can be imposed even on some neutral hydrophilic monomers containing hydroxylic groups: For example hydroxylic groups introduced in the copolymer by the 2-hydroxyethyl methacrylate monomer can partly be transformed in operative mercapto groups by treatment of the copolymer with thiourea in the presence of hydrochloric acid and by subsequent alcaline decomposition of primarily formed thiuronium groups. The hydroxylic functions can be activated in the well known way for the coupling with aminogroups of the component $b$ even by treatment with bromocyanogen in the same way as was applied for the activation of SEPHADEX dextrane carriers. Moreover bromocyanogen activated dextrane carriers of the SEPHADEX type themselves can be applied as a component a.

Some operative monomers can introduce in the component a functional groups which without any chemical aftertreatment of the polymer can play the role of a ligand to complementary ligands of the component b. Examples of such monomers are methacryloylvaniline introducing the reactive aldehydic group or m-isothiocyanatostyrene introducing the isothiocyanate group into the copolymer.

The water soluble second order carrier (component b) may be comprised of the copolymerization product of a hydrophilic monoolefinic monomer such as acrylic, methacrylic or itaconic acids, N-lower alkyl substituted acrylamides, lower alkylenglycol monomethacrylate or acrylate, acrylamide, methacrylamide and the like with an operative monomer providing similar functionalities like operative monomers used for the synthesis of first order carriers.

Cross-linking monomers are not added in this case and if they are present as impurities e.g. small amounts of glycol diacrylate in glycol monoacrylate, their cross-linking action should be compensated by the chain transfer reaction of a solvent e.g. ethanol in order to obtain a water soluble polymer. The weight ratio of the hydrophilic monoolefinic monomer to the operative monomer will generally be about 1 : 0.005 to 1 : 25, preferably 1 : 0.01 to 0.10.

The final equippment of both components a and b with ligands which enables the chemical coupling of these components to form eventually the carrier is illustrated in Table I.

the instant invention include such materials as enzymes, enzyme inhibitors, antigens and antibodies.

Thus, for example, the secondary carrier may be prepared by copolymerization of acrylamide with methacrylanilide and mercurated by mercuric acetate at its anilide benzene rings (according to Czechoslovak Pat. No. 803 717 (Application PV 5742-72)) and can be linked to the surface of wool, silk or reprecipitated collagen by bonds to the cystein units of these proteins, or can be bound to a surface of the Sepharose mercapto derivative. A carrier is formed in these cases which retains the macroscopic structure and mechanical properties of the primary carrier and also has solvated long linear macromolecules at its surface and at the same time carries mercuryanilide units in shorter or longer intervals able to bind water soluble proteins containing sulfhydryl units, e.g. pepsin.

The following examples illustrate the invention without, however, limiting its scope. All parts proportions and ratios therein as well as in the appended claims are by weight unless otherwise indicated.

EXAMPLE 1

Diethylene glycol monomethacrylate (35 weight parts), 2.6 wt. parts of 2-(p-acetaminophenoxy) ethyl methacrylate and 2 wt. parts of 2,2-azobisisobutyronitrile are dissolved in 150 wt. parts of 90% ethanol and refluxed for 3 hours. The cooled reaction mixture is then mixed with 100 wt. parts of water and distilled in vacuo to remove about 100 wt. parts of the water - ethanol mixture. Another 100 wt. parts of water is added to the residue and 100 wt. parts are distilled off again in the same way. The distillation residue after the second vacuum distillation is heated with the concentrated aqueous solution containing 2 wt. parts of NaOH

| Example | ligands of component a to couple with component b | ligands of component b to couple with component a | ligands of coupled component b transformed to couple with biomaterials |
|---|---|---|---|
| 1 | $-Ar-N_2^+$ | $-Ar-NH_2$ | $-Ar-N_2^+$ |
| 2 | $-Ar-N_2^+$ | $-Ar-NH_2$ | $-Ar-N=C=S$ |
| 3 | $-Ar-N_2^+$ | $-CO-NH-Ar$ | $-CO-NH-Ar-Hg^+$ |
| 4 | $-Ar-N_2^+$ | $-Ar-NH_2$ | $-Ar\begin{cases}NH_2\\Hg^+\end{cases}$ |
| 5 | $-N=C=S$ | $-CO-NH-NH_2$ | $-CO-N_3$ |
| 6 | $-CH=O$ | $-CO-NH-NH_2$ | $-CO-N_3$ |
| 7 | $-Ar-OH$ | $-Ar-N_2^+$ | $-Ar-N_2^+$ |
| 8 | $-Ar-N(CH_3)_2$ | $-Ar-N_2^+$ | $-Ar-N_2^+$ |
| 9 | $-SH$ | $-Ar-Hg^+$ | $-Ar-Hg^+$ |
| 10 | $-NH_2$ | $-N=C=S$ | $-N=C=S$ |
| 11 | $-NH_2$ | $-NH-\underset{F}{\underset{\|}{C_6H_3}}(O_2N)(NO_2)$ | $-NH-\underset{F}{\underset{\|}{C_6H_3}}(O_2N)(NO_2)$ |
| 12 | $-CO-NH-NH_2$ | $-CH=O$ | $-CH=O$ |

In the most simple case (examples 7 - 12) the active ligand of the component a are of the same kind as ligands required for the fixation of bioactive materials. In other cases (examples 1 - 6) the ligands of the component b should be modified chemically after both components a and b have been coupled, in order to obtain ligands capable to form covalent bonds with biological materials.

The various biologically active materials which may be carried by the product produced in accordance with for 40 minutes on a steam bath. The reaction mixture is then cooled, and neutralized with dilute hydrochloric acid (1:1) to a pH of 7. The neutral solution of the polymer (secondary carrier) is filtered through a layer of charcoal and used for the subsequent binding to the primary polymeric carrier.

Hydroxyethyl methacrylate gel (25 wt. parts) cross-linked with 40% ethylene dimethacrylate, containing 5% of 2-(p-acetaminophenoxyl)ethyl methacrylate in its three-dimensional structure and having a molecular weight exclusion limit of 300 000 is used as the primary carrier and is swollen in distilled water over night. Excessive water is sucked off on a sintered-glass filter and the remaining gel is heated in 250 wt. parts of 5% aqueous NaOH to 100° C for 2 hours to complete cleavage of the acetamide bond at the aromatic ring. After hydrolysis, the product is washed on a sintered-glass filter until any alkaline reaction ceases. The swollen hydrolyzed gel is stirred into 50 wt. parts of 1N HCl solution and cooled to 0° C. 50 wt. parts of a cold 1N NaNO$_2$ solution is then gradually added in small portions. After the entire amount has been added, the gel is left to stand in a refrigerator for 2 hours at 0° C and then washed with distilled water until the nitrite reaction is absent. The swollen diazotized gel is then mixed with the linear copolymer of diethylene glycol monomethacrylate with 2-(p-acetaminophenoxyl) ethyl methacrylate (secondary carrier) at a pH of 8 and left to react for 2 hours at ambient temperature. After thorough washing with water, the unreacted diazonium chloride groups at the primary carrier are coupled with 5 wt. parts of β-naphthol in 200 wt. parts of water containing 1 wt. part of NaOH. After further washing until any alkaline reaction ceases, the secondary carrier fixed to the gel is diazotized with 50 wt. parts of sodium nitrite in 50 wt. parts of hydrochloric acid using conditions analogous to those of the diazotizing of the primary carrier. After washing to a neutral reaction using iodine-starch paper and a pH of 7, chymotrypsin is bound to the secondary carrier at ambient temperature.

The immobilized enzyme exhibits high esterase and proteolytic activities.

EXAMPLE 2

The secondary carrier is bound to the primary carrier as described in Example 1 and the aminophenyl groups of the secondary carrier are mercurated with a saturated solution of mercuric acetate (100 wt. parts) for 3 hours on a steam bath. After thorough washing, the proteolytic enzyme papain is bound to the gel.

EXAMPLE 3

A solution of the secondary carrier prepared according to Example 1 and containing 4 wt. parts of the dry substance in 17 wt. parts of water is treated with 5 wt. parts of 10% NaNO$_2$ solution and 5 wt. parts of diluted HCl (1:3) in a china mortar. A sticky white precipitate separates immediately after addition of the acid and then thoroughly worked in a mortar so as to achieve good contact of both phases. The aqueous layer is decanted and the polymer is thoroughly extracted by kneading with 7M NaH$_2$BO$_4$ solution. The polymer is then dissolved in 30 wt. parts of water; the resulting solution gives no reaction with iodine-starch paper, which is evidence of the substantially complete washing from the unreacted nitrite.

The primary carrier is prepared by suspension copolymerization of 48 wt. parts of 2-hydroxyethyl methacrylate, 32 wt. parts of ethylene dimethacrylate and 1.6 wt. parts of methacrylanilide in the presence of 98 wt. parts of cyclohexanol, 10 wt. parts of lauryl alcohol and 1 wt. part of 2,2-azobisisobutyronitrile in 600 wt. parts of water and stabilization of the suspension with 6 wt. parts of poly(vinylpyrrolidone). The suspension copolymer obtained is then roughly washed with methanol and water, dried and fractionated using screens, according to particle size; the fraction having a size of 200 –300μ is used.

The primary polymeric carrier is swollen in a universal borate buffer solution (pH 7.5) mixed with 30 wt. parts of the solution of diazotized secondary carrier and left to stand at the ambient temperature for 24 hours. After washing with water, the gel reacts with chymotrypsin at a pH of 8 giving the active immobilized enzyme.

We claim:

1. A method for the production of carriers for binding biologically active compounds comprising admixing
   (a) a primary component comprising a three-dimensional water insoluble polymer of components: (i) at least one monomer selected from the group consisting of lower alkyl acrylates and methacrylates, lower hydroxyalkyl acrylates and methacrylates and diethylene glycol and glycerol monoacrylates and monomethacrylates; (ii) a cross-linking agent selected from the group consisting of lower alkylene glycol diacrylates and dimethacrylates, allyl methacrylate, glycerol dimethacrylate, butantetrol dimethacrylate and N,N'-methylene-bisacrylamide; and (iii) an operative monomer selected from the group consisting of acrylic and methacrylic compounds containing a phenolic or aromatic amine function; and
   (b) a secondary component comprising a water-soluble polymer of a hydrophilic monoolefinic monomer selected from the group consisting of acrylic acid, methacrylic acid, itaconic acid, N-lower alkyl substituted acrylamides, lower alkylene glycol monomethacrylates and acrylates, acrylamide and methacrylamide, said water-soluble polymer containing an aromatic diazonium group, for a time sufficient to cause said diazonium group to form covalent bends with said primary component.

2. The method of claim 1, wherein said monomer (a) (i) is 2-hydroxyethyl methacrylate.

3. The method of claim 1, wherein said cross-linking agent is ethylene glycol dimethacrylate.

4. The method of claim 1, wherein said operative monomer is methacryloylanilide.

5. The method of claim 1, wherein said operative monomer is 4-amino-acryloylanilide.

6. The method of claim 1, wherein said operative monomer is p-aminophenoxyethyl methacrylate.

7. The method of claim 1, wherein said secondary component is formed from diethylene glycol monomethacrylate and 2-(p-acetaminophenoxy) ethyl methacrylate.

8. A carrier for biologically active materials produced by the method as defined in claim 1.

* * * * *